(12) United States Patent
Mandic

(10) Patent No.: US 8,614,331 B2
(45) Date of Patent: Dec. 24, 2013

(54) PROCESS FOR PREPARATION OF ESOMEPRAZOLE SODIUM OF HIGH CHEMICAL PURITY AND NEW FORMS OF ESOMEPRAZOLE SODIUM

(75) Inventor: Dejan Mandic, Ljubljana (SI)

(73) Assignee: Lek Pharmaceuticals D.D., Ljubljana (SI)

( * ) Notice: Subject to any disclaimer, the term of this patent is extended or adjusted under 35 U.S.C. 154(b) by 197 days.

(21) Appl. No.: 13/001,936

(22) PCT Filed: Jul. 8, 2009

(86) PCT No.: PCT/EP2009/058650
§ 371 (c)(1),
(2), (4) Date: Mar. 21, 2011

(87) PCT Pub. No.: WO2010/003974
PCT Pub. Date: Jan. 14, 2010

(65) Prior Publication Data
US 2011/0166183 A1    Jul. 7, 2011

(30) Foreign Application Priority Data

Jul. 9, 2008 (EP) .................................. 08159993

(51) Int. Cl.
*C07D 401/12* (2006.01)
(52) U.S. Cl.
USPC ..................................................... 546/273.7
(58) Field of Classification Search
USPC ........................................ 546/273.7; 514/338
See application file for complete search history.

(56) References Cited

U.S. PATENT DOCUMENTS 6,627,646 B2 * 9/2003 Bakale et al. ................. 514/322
2007/0259921 A1 11/2007 Bolugoddu et al.

FOREIGN PATENT DOCUMENTS

WO    WO 2005/105786 A1    11/2005
WO    WO 2005/116011 A1    12/2005

OTHER PUBLICATIONS

CMU Pharmaceutical polymorphism, internet p. 1-3 (2002) printout Apr. 3, 2008.*
Singhal et al., "Drug Polymorphism, etc.," Advanced Drug Delivery reviews 56, p. 335-347 (2004).*
Concise Encyclopedia Chemistry, NY: Walter de Gruyter, 1993, 872-873.*
Jain et al., "Polymorphism in Pharmacy", Indian Drugs, 1986, 23(6) 315-329.*
Muzaffar et al., "Polymorphism and Drug Availability, etc.," J of Pharm. (Lahore), 1979, 1(1), 59-66.*
U.S. Pharmacopia #23, National Formulary #18, 1995, 1843-1844.*
Doelker, english translation of S.T.P, Pratiques (1999), 9(5), 399-409, pp. 1033.*
Doelker, english translation of Ann. Pharm. Fr., 2002, 60: 161-176, pp. 1-39.*
Taday et al., "Using Terahertz, etc.," J of Pharm. Sci., 92(4), 2003, 831-838.*
Otuska et al., "Effect of Polymorphic, etc.," Chem. Pharm. Bull., 47(6) 852-856 (1999).*

* cited by examiner

*Primary Examiner* — Patricia L Morris
(74) *Attorney, Agent, or Firm* — Arent Fox LLP

(57) ABSTRACT

A process for preparing esomeprazole sodium comprises the steps of providing a solution of esomeprazole sodium in a solvent constituted mainly of methanol or only of methanol; and carrying out precipitation or crystallization of esomeprazole sodium from said solution. Esomeprazole sodium is preferably obtained from pure form of neutral racemate through chiral chromatography using methanol-based mobile phase, and a subsequent reaction with sodium source. Novel crystal and semicrystal forms of esomeprazole sodium can be provided repeatedly and in physically stable and highly pure form.

4 Claims, 7 Drawing Sheets

PROCESS FOR PREPARATION OF ESOMEPRAZOLE SODIUM OF HIGH CHEMICAL PURITY AND NEW FORMS OF ESOMEPRAZOLE SODIUM

CROSS-REFERENCE TO RELATED APPLICATION

This application is a 371 National Stage entry of International Application No. PCT/EP2009/058650, filed Jul. 8, 2009, now WO 2010/003974 with an International Publication date of Jan. 14, 2010, which claims the benefit of priority to EP 08159993.8, filed Jul. 9, 2008, the entire specification, claims and drawing of which are incorporated herewith by reference.

FIELD OF THE INVENTION

The present invention belongs to the field of pharmaceutical industry and relates to a novel procedure of preparation esomeprazole sodium salt of high chemical purity and its incorporation into a final dosage form. The process of the invention also discovers two novel crystal forms of sodium salt of esomeprazole.

BACKGROUND OF THE INVENTION

The compound omeprazole (5-methoxy-2-[[(4-methoxy-3,5-dimethyl-2-pyridinyl)methyl]sulfinyl]-1H-benzimidazole) is well known as an effective gastric acid secretion inhibitor and is useful as an anti-ulcer agent. Omeprazole has two enantiomeric forms R-omeprazole and S-omeprazole shown below and normally exists as a racemic mixture. The S-enantiomer commonly referred to as esomeprazole is said to have improved pharmacokinetic properties which give an improved therapeutic profile such a lower degree of inter-individual variation (see WO 94/27988).

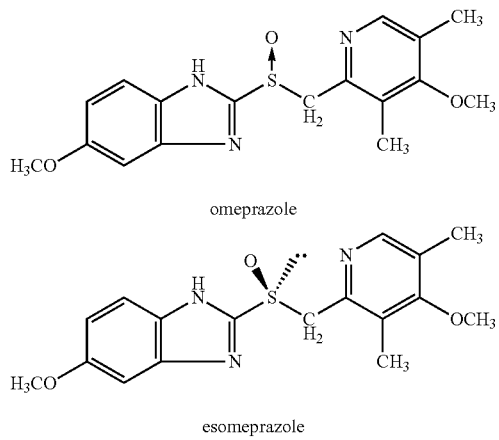

omeprazole esomeprazole

Enantiomers and their mixtures, including racemates behave identically or similarly in achiral environment in view of chemical reactivity and physical properties of liquid and gaseous state. But physico-chemical properties of solid state forms of racemates and enantiomers differ significantly and they cannot be automatically predicted from one to the other. For instance, racemic omeprazole in neutral form is well crystalline compound while neutral esomeprazole is often semisolid and needs special treatment to obtain easily insoluble and stable crystals (WO 98/28294). Consequently pharmaceutically applicable form of esomeprazole is its magnesium salt (WO 98/54171) which is better crystalline than neutral form which is the main market form of racemic omeprazole. Not easily available solid state means also lack of an efficient purification tool for purification by recrystallisation. Racemic neutral omeprazole of very high chemical purity over 99.94% can be reached in a relatively simple way (U.S. Pat. No. 6,191,148) while the purification of esomeprazole needs other approaches. One of most efficient tools is well crystalline potassium salt which is used for preparation of magnesium salt of esomeprazole in many literature sources (WO 00/44744, WO 06/001753).

Esomeprazole can be prepared by enantioselective chemical reaction or by separation of S-enantiomer from racemate. Catalytic enatioselective oxidation of prochiral sulphide was first disclosed in WO 96/02535. Relatively complex mixture of reagents in this reaction and in later published alternative approaches needs an efficient purification method in order to eliminate inorganic and organic impurities especially over-oxidated sulfone. Separation of enantiomers by diastereomeric derivatives is disclosed in WO 92/08716 and WO 05/105786. Cleaving of derivatising group can produce new impurities which must be removed. Separation by chiral chromatography is also described (WO 05/105786, WO 07/071, 753).

Injectable forms of omeprazoles use sodium salt due to their excellent solubility in water. Sodium salt of racemic omeprazole of high purity can be simply prepared from very pure neutral form and only care how to make the most stable physical form should be taken. Because very pure neutral form of esomeprazole is less accessible analogous procedure for esomeprazole sodium cannot be performed. Procedure from very pure potassium salt by direct reprecipitation is very suitable in preparation of magnesium salt (WO 05/105786) while such procedure fails in preparation of sodium salt due to better solubility of sodium salt. Reacidification of a salt to make a neutral intermediate should be done, but this readily reproduces new impurities, because omeprazole is unstable in acidic condition and at least colorification happens.

Esomeprazole sodium was first disclosed in WO 94/027988 preparing it from crude esomeprazole in toluene-2-butanone mixture after separating derivatized diastereoisomers and removal of derivatizing group in acidic conditions. Toluene is not very suitable solvent for the last step and the method does not guarantee removal of inorganic impurities.

WO 01/014367 describes a preparation of esomeprazole sodium in THF from crude esomeprazole after enantioselective oxidation. The solvent has similar deficiencies like toluene.

WO 03/089408, WO 04/052882 and WO 07/013,743 disclose preparation of esomeprazole sodium from methyl isobutyl ketone and tried to purify the crude material by crystallisation from acetone or digesting in acetonitrile respectively. Purities 99.8% and 85% are reached.

WO 06/001753 discloses preparation of three novel crystal forms starting from potassium salt. After acidification in order to obtain neutral esomeprazole toluene again is used. WO 06/001755 describes preparation of another new polymorph B but the procedure is not industrially applicable. It applies natural evaporation of water from extremely concentrated water solution.

Patent application US 2007/0259921 shows the first preparation of very pure esomeprazole but is silent about very pure starting neutral esomeprazole and its significance. Furthermore Form J which is the most pure form easily converts to Form K, but the interchangeability between physical forms does not guarantee a repeatable process. Other described forms are less pure.

Therefore it is still need for preparation of highly pure esomeprazole sodium by a repeatable process which guarantees stable physical form.

SUMMARY OF THE INVENTION

The present invention provides the following aspects, subject-matters and preferred embodiments, which respectively taken alone or in combination significantly contribute to the preparation of highly pure esomeprazole sodium in a repeatable manner, and providing stable physical form of esomeprazole sodium.

(1) A form of esomeprazole sodium, which is semicrystalline by showing in a XRD diffractogram a single significant peak at a 2θ value of 5.7 while the rest of the curve is plain without significant peaks, preferably being characterized by an XRD diffractogram as shown in FIG. 3.

The term "without significant peaks" used herein means that, besides the indicated single significant peak, a XRD diffractogram does not show peaks typical for crystal structures, but rather a curve line typical for amorphous substances.

This form is denoted "Form Q" and is indicative for, and more specifically shows a non-limiting example of a particular form of crystalline esomeprazole sodium derivable from the conversion of the form defined in item (3) or (4) below, preferably Form P, into an exceptionally pure and physically stable form of crystalline esomeprazole sodium having a peculiar semicrystalline crystal structure.

(2) The form of esomeprazole sodium according to item (1), defined by a HPLC purity of at least 99.00%, preferably at least 99.90% and more preferably at least 99.95%. This preferred form is indicative of the fact that with the Form Q provided by the present invention, it is possible to achieve an exceptionally pure form of esomeprazole sodium.

(3) Crystal form of esomeprazole sodium comprising 5-15 wt.-% methanol, preferably 8-10% methanol. Methanol content can be determined by assay (typically by GC determination).

According to this aspect of the present invention, it has been surprisingly found that a crystal form of esomeprazole sodium comprising controlled but substantial amount of methanol ensures reproducibility and maintenance of beneficial crystal structure, thereby avoiding interchanges between various forms of esomeprazole sodium.

The crystal form of the present aspect of the invention may further comprise a different solvent substance other than methanol, e.g. selected from co-solvents, functional additive or anti-solvents such as esters and ethers mentioned above, or a mixture thereof, but usually at an amount lower than methanol. Yet, though providing crystal structure protection, the crystal form of the present aspect of the invention can be efficiently converted into another novel, physically stable and exceptionally pure esomeprazole sodium.

(4) Crystal form of esomeprazole sodium which is characterized by peaks at 2θ values of 6.2; 14.7; 15.5; 16.3; 18.5; 23.2; 24.0; 24.9 in XRD diffractogram, respectively exactly or ±0.2 degrees 2θ at the indicated 2θ values, preferably being characterized by an XRD diffractogram as shown in FIG. 1.

This form is denoted "Form P" and is indicative for, and more specifically shows a non-limiting example of a particular form of crystalline esomeprazole sodium, in particular one derivable from methanol solvation as defined in item (3) above.

(5) Use of the crystal form of item (3) or (4) as intermediate for the preparation of highly pure esomeprazole sodium.

The term "highly pure" used herein means a chemical or chromatographic (area % HPLC) purity of at least 99.00%, preferably at least 99.90%, more preferably at least 99.95%. The term includes a purity reaching up to practically 100.0 area % chromatographic purity. The term "highly pure" may also include a characteristic that the level of solvent, in particular methanol, is reduced, preferably to a level below 0.5% (w/w).

(6) A preparation of esomeprazole sodium comprising a mixture of any one of the forms defined in items (1) to (4) above.

(7) A process for preparing esomeprazole sodium comprising the steps of:
providing a solution of esomeprazole sodium in a solvent constituted mainly of methanol or only of methanol; and
carrying out precipitation or crystallisation of esomeprazole sodium from said solution.

This procedural concept according to one aspect of the invention can provide novel crystalline forms of esomeprazole sodium, including particular forms such as Form P and Form Q further described herein, but can exclude Forms J, K, L, N and other previously known Forms mentioned above if such conventional Forms are not desired.

The term "solvent constituted mainly of methanol" used herein means more than 50 v/v-%, preferably more than 75 v/v-%, more preferably essentially methanol of at least 99 v/v-%. The remainder of the solution phase may include suitable co-solvent, such as other alkanol like ethanol, propanol, butanol, tert-butyl alcohol, isopropyl alcohol, water; anti-solvent such as methyl tert-butyl ether, diethyl ether and ethyl acetate; functional additive such as those described in more detail below; and the like. The solvent may preferably be constituted of a mixture of mainly methanol and ethanol as a remainder, more preferably of methanol only, optionally supplemented with functional additive only.

According to this concept of the invention, methanol solvate and/or methanol adduct of esomeprazole sodium can be formed. The obtainable crystalline product contains controlled, but substantial amounts of methanol which acts as stabilizing surrounding to keep crystal structure. Furthermore, the methanol solvate or adduct of esomeprazole sodium can be reliably and repeatedly transformed into other stable and non-interchangeably crystal forms, in particular Form Q described below.

(8) The process according to item (7), wherein the esomeprazole sodium had been previously prepared from neutral racemic omeprazole by chiral column chromatography using a mobile phase constituted mainly of methanol or only of methanol.

The term "mobile phase constituted mainly of methanol" used herein means more than 50 v/v-%, preferably more than 75 v/v-%, more preferably essentially methanol of at least 99 v/v-%. The remainder of the mobile phase may be suitable co-solvent, such as other alcanol like ethanol, propanol, butanol, tert-butyl alcohol, isopropyl alcohol, water; functional additive such as those described in more detail below; and the like. The mobile phase may preferably be constituted of a mixture of mainly methanol and ethanol as a remainder, more preferably of methanol only, optionally supplemented with functional additive only.

The chiral chromatography practically completely removes unwanted R-enantiomer. This provision of enantiomeric pure esomeprazole preferably by chiral chromatography can be advantageously combined with the basic concept according to item (7) above, because methanol-based solutions and especially methanol only as a mobile phase already ensures proper solvent surrounding of esomeprazole for its further processing according to the present invention. In methanol-based solutions neutral esomeprazole can be readily converted into esomeprazole sodium and further processed as will be described below.

(9) The process according to item (7) or (8), wherein esomeprazole sodium is obtained by contacting neutral esomeprazole with sodium source, preferably wherein neutral esomeprazole is contacted with sodium source dissolved in methanol. This ensures reliable, robust and efficient conversion of neutral form into sodium salt form of esomeprazole.

(10) The process according to any one of items (7) to (9), wherein the solution of esomeprazole sodium in methanol is concentrated before carrying out the precipitation or crystallisation step. This measure provides for an efficient precipitation or crystallisation, starting even at room temperature if desired, and surprisingly directly from the solution comprising mainly or only methanol without requiring addition of other solvents.

(11) The process according to any one of items (7) to (10), wherein an esomeprazole sodium seed crystal is used for crystallisation. This process increases crystallisation efficiency and formation of desired crystal form. For example and preferably, seeds of crystalline Form P of the present invention are effective to form exceptionally pure esomeprazole sodium Form P.

(12) The process according to any one of items (7) to (11), wherein the step of precipitation or crystallisation is performed from a solution described above which is concentrated by comprising 100 to 1000 g/L, preferably 200 to 500 g/L and more 250 to 350 g/L esomeprazole sodium. Efficient precipitation or crystallisation is made possible, surprisingly even without adding new solvent such as a previously suggested (anti)solvent.

(13) The process according to any one of items (7) to (12), wherein the step of precipitation or crystallisation is performed under a treatment of ultrasonic radiation. In this way, it is possible to directly yield Form Q of the present invention from the—optionally concentrated—solution described above.

(14) A process for preparing of esomeprazole sodium, comprising the following steps:
a) providing neutral racemic omeprazole,
b) separation of enantiomers of the neutral racemic omeprazole by chiral column chromatography using a mobile phase constituted mainly of methanol or only of methanol,
c) concentration of fractions containing esomeprazole (eluates) obtained from the chiral column chromatography,
d) addition of a source of sodium to the concentrated fractions of step c),
e) after step d) optionally additional concentration or/and optionally addition of a new solvent selected from esters and ethers or mixture of them,
f) precipitation or crystallisation of the sodium salt from the liquor obtained after step d) or e),
g) recovering esomeprazole sodium after step f).

This aspect of the present invention provides particularly efficient combination of process steps to repeatedly arrive at pure and physically stable esomeprazole sodium starting from neutral racemic omeprazole.

As to the mobile phase constituted mainly of methanol or only of methanol, reference is made to the description of item (8) above.

(15) The process according to (14), wherein for the step of separating enantiomers neutral racemic omeprazole is loaded onto the chiral chromatography column dissolved in methanol as the main or the only solvent.

As to the solvent constituted mainly of methanol or only of methanol, reference is made to the description of item (7) above.

(16) The process according to item (14) or (15), wherein the step of recovering includes
isolation of the precipitated or crystallised solid mass, preferably by filtration or centrifugation,
optionally drying the solid mass, preferably at reduced pressure.

(17) The process according to any one of the preceding items (7) to (16), wherein neutral racemic omeprazole or neutral esomeprazole is used as starting compound having a chemical purity of at least 99.0%, preferably at least 99.8% and more preferably at least 99.9%.

It has been surprisingly found that if one does not pay attention to starting with such high purity, residual amounts of impurities can not anymore be surely removed in the final steps dealing with esomeprazole sodium, e.g. the final precipitation or crystallisation step or other purification or isolation steps, and thereby such residual amounts of impurities inevitably still remain. When the already essentially pure starting compound is used as indicated, furthermore the later solvent selection can be optimized with respect to the yielded crystal form, rather than making compromise between crystallisation/precipitation requirements and separating off impurities.

(18) The process according to any one of the preceding items (7) to (17), wherein a base substance is added to the methanol-based solvent or mobile phase as a functional additive, preferably at an amount of not more than 0.1 v/v %, more preferably not more than 0.05 v/v %. Preferably an amine compound, more preferably alkylamines and most preferably diethylamine is used.

This preferred embodiment protects against acid catalysed decomposition of racemic omeprazole starting compound or esomeprazole during processing.

(19) A process for modifying the form of esomeprazole sodium by drying a prepared esomeprazole sodium at reduced pressure in an atmosphere containing water vapour.

According to this beneficial aspect of the present invention, a form of esomeprazole sodium, suitably selected from premature crystalline forms, solvated forms, adduct forms, hydrate forms or the like, can be gently converted by this careful and controlled wet drying into improved forms selected from matured, stable, solvate-free, adduct-free forms, forms containing modified water content of crystalline esomeprazole sodium, and especially forms of crystalline esomeprazole sodium having increased purity, more preferably being exceptionally pure. While conversions of other forms of esomeprazole sodium are feasible, this process is preferably applicable for the conversion of Form P into Form Q. This process according to the present invention is preferably performed in an inert atmosphere, for example a flow of nitrogen gas saturated with moisture. In this advantageous aspect to the invention, it is ensured that a previously observed chemical/chromatographic purity does not drop down.

(20) A pharmaceutical preparation comprising the form of esomeprazole according to any one of items (1) to (4) and (6) and a pharmaceutically acceptable excipient.

(21) A pharmaceutical preparation comprising the esomeprazole sodium as prepared by a process according to any one of items (7) to (18) and a pharmaceutically acceptable excipient.

(22) A use of the form of esomeprazole sodium according to any one of items (1) to (4) and (6), or of the pharmaceutical preparation according to item (20) or (21) for the manufacture of a medicament for prevention and/or for treatment of a gastrointestinal inflammatory disease or condition. The esomeprazole sodium forms and the pharmaceutical preparation according to the present invention is particularly suitable as anti-ulcer agent.

(23) A use of esomeprazole sodium as prepared by a process according to any one of items (7) to (18) for the manufacture of a medicament for prevention and/or treatment of a gastrointestinal inflammatory disease or condition.

(24) The use according to item (23), wherein the medicament is manufactured by dissolving or dispersing the form of esomeprazole sodium according to any one of items (1) to (4) and (6), or the pharmaceutical preparation according to item (20) or (21), in aqueous medium, lyophilizing the solution or dispersion to obtain the pharmaceutical product.

Preferably the aqueous medium is sterile and apyrogen water, and more preferably a at least one substance selected from stabilisers, buffers and additives are added to the aqueous medium, and the mixture is lyophylised to give vials of amorphous powder which is dissolved in prepared liquid just before use.

DETAILED DESCRIPTION OF THE INVENTION

Figure 1:
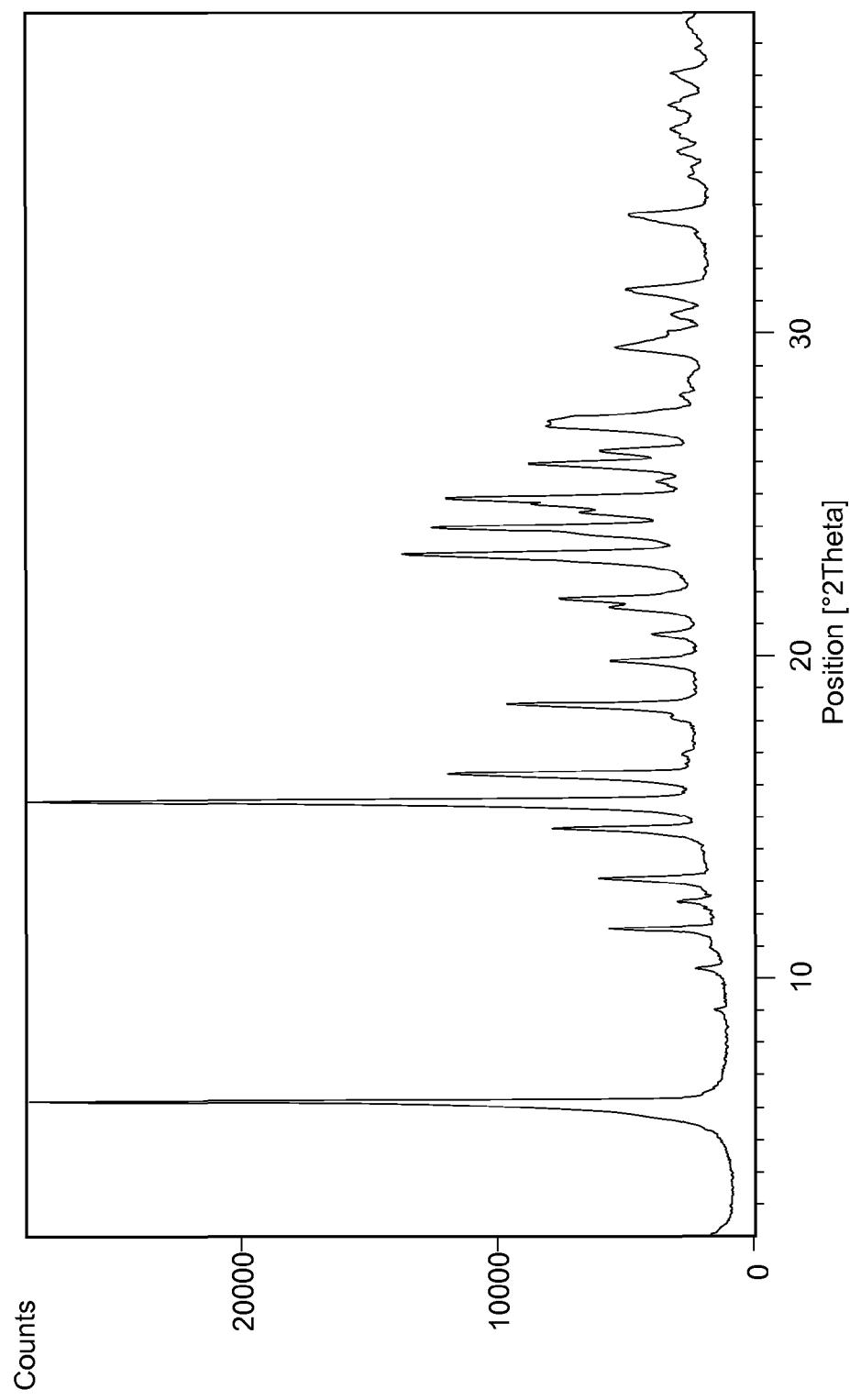
FIG. 1 is an X-Ray powder diffractogram of esomeprazole sodium Form P.

Significant advantages of the present invention reside in that novel crystal and semicrystal forms of esomeprazole sodium can be provided repeatedly and in physically stable and highly pure form.

The present invention is now described in more detail by referring to further preferred and further advantageous embodiments and examples, which are however presented for illustrative purposes only and shall not be understood as limiting the scope of the present invention.

A preferred, particular embodiment of the process of the invention relates to a preparation of esomeprazole sodium starting from neutral racemic omeprazole of chemical purity at least 99.9% and including the following steps:
  separation of its enantiomers by chiral column chromatography using methanol as a mobile phase,
  concentration of main fractions (eluates),
  addition of a source of sodium to the concentrated fractions,
  precipitation of the sodium salt from the solution optionally after additional concentration or/and with optional addition of a new solvent selected from esters and ethers or mixture of them,
  isolation of the separated solid mass by filtration,
  drying the solid mass at reduced pressure in the atmosphere of water vapours A starting neutral omeprazole of purity at least 99.9% is commercially available.

Preferred chromatographic separation of omeprazole into its enantiomerically pure or optically enriched isomers can be achieved by application of column chromatography with chiral stationary phase (CPS) capable of chiral recognition and solvent desorbent (mobile phase). It was presented as a feasible method in patent applications WO 03/051867 and WO 07/071,753. As a mobile phase the last reference uses unique solvent methanol as highly advantageous but the whole process of isolation is focused to preparation of magnesium salt which is less soluble in methanol as the sodium salt. Isolation of esomeprazole sodium from methanol has not been known, yet. Previously it was considered that methanol should be replaced by another solvent by complete removal of methanol through evaporation and adding the second solvent to the residue or by co-distillation with the second solvent (US 2007/0259921).

Thus the process of the present embodiment advantageously applies a chromatographic system with polysaccharide coated CPS (ChiralPak AD) as a stationary phase and a mobile phase constituted of mainly methanol and preferably only methanol. The esomeprazole obtained from the chiral chromatography can then be processed further in the methanol-based solution as described. By using methanol-based mobile phase in PHPLC resolution good selectivity of omeprazole enantiomers is obtained and also high solubility of omeprazole samples in mobile phase is provided. These mobile phase properties allow higher concentration of the samples that are injected on the column, therefore higher loading capacity and efficiency of the separation. The system provides very high retention time reproducibility and main fraction can be collected according to fixed time window. The separation of enantiomers depends on the length of the column; the length of 350 mm practically completely removes R-enantiomer, preferably at least 99.7% of enantiomeric purity should be reached. Furthermore the column additionally removes also some of other chemically impurities. For example it enhances the chemical purity from 99.90% in starting omeprazole to 99.95% and above in the eluate.

Neutral omeprazole and esomeprazole are unstable in the presence of even catalytic amounts of acids. In order to ensure longer stability and to keep high chemical purity a slight amount of a base is preferably added. Preferably alkylamines are used, more preferably diethylamine is added, respectively in a small amount of preferably not more than 0.1 v/v %, most preferably not more than 0.05 v/v %.

The collected eluates of S-omeprazole are then preferably concentrated to a smaller volume by distillation of the solvent, preferably to concentrations of 50 to 500 g/l, most preferably 100 to 300 g/l. Then, it is preferred that a methanol solution of sodium source, suitably selected from sodium methoxide and sodium hydroxide, is added to the concentrate of neutral S-omeprazole. Solution of sodium methoxide can be effectively prepared by dissolving of solid sodium methoxide, higher alcoxide preferred t-butoxide, sodium amide or silylated amide, sodium hydride in methanol or by reacting methanol with elemental sodium. Preferably, sodium source such as sodium methoxide or sodium hydroxide in the amount of 0.9-1.5 eq per esomeprazole, preferably 1.0-1.1 eq. is used. The mixture can be stirred at temperature between 10° C. and 40° C., preferably at room temperature. The reaction time may be ranging between 10 minutes and 2 hours, preferably the reaction time is between 0.5 and 1 hour.

The obtained solution is then preferably reconcentrated to the same volume as before the reaction, preferably below 250 g/l. Contrary to what would be expected from previous literature, esomeprazole sodium begins to precipitate without addition of a new solvent at room temperature. To enhance precipitation, the mixture is then preferably cooled to below 15° C., preferably below 0° C. and stirred 15 min to 10 h, preferably from 0.5 to 1 h. Crystals can be finally filtered off or centrifuged off and dried under reduced pressure at temperature 20-45° C., preferably at 30-35° C.

We surprisingly found that the obtained crystal form is different from any known form, furthermore it is different from all crystal forms obtained from methanol including media (Form C described in WO 06/001753 and Forms J, K, L, M, N, described in US 2007/0259921). The particularly preferred new form, named as form P, shows clear diffractions in XRD diffractograms, shown in FIG. 1 characterized by 2θ values of 6.2; 14.7; 15.5; 16.3; 18.5; 23.2; 24.0; 24.9.

Figure 5:
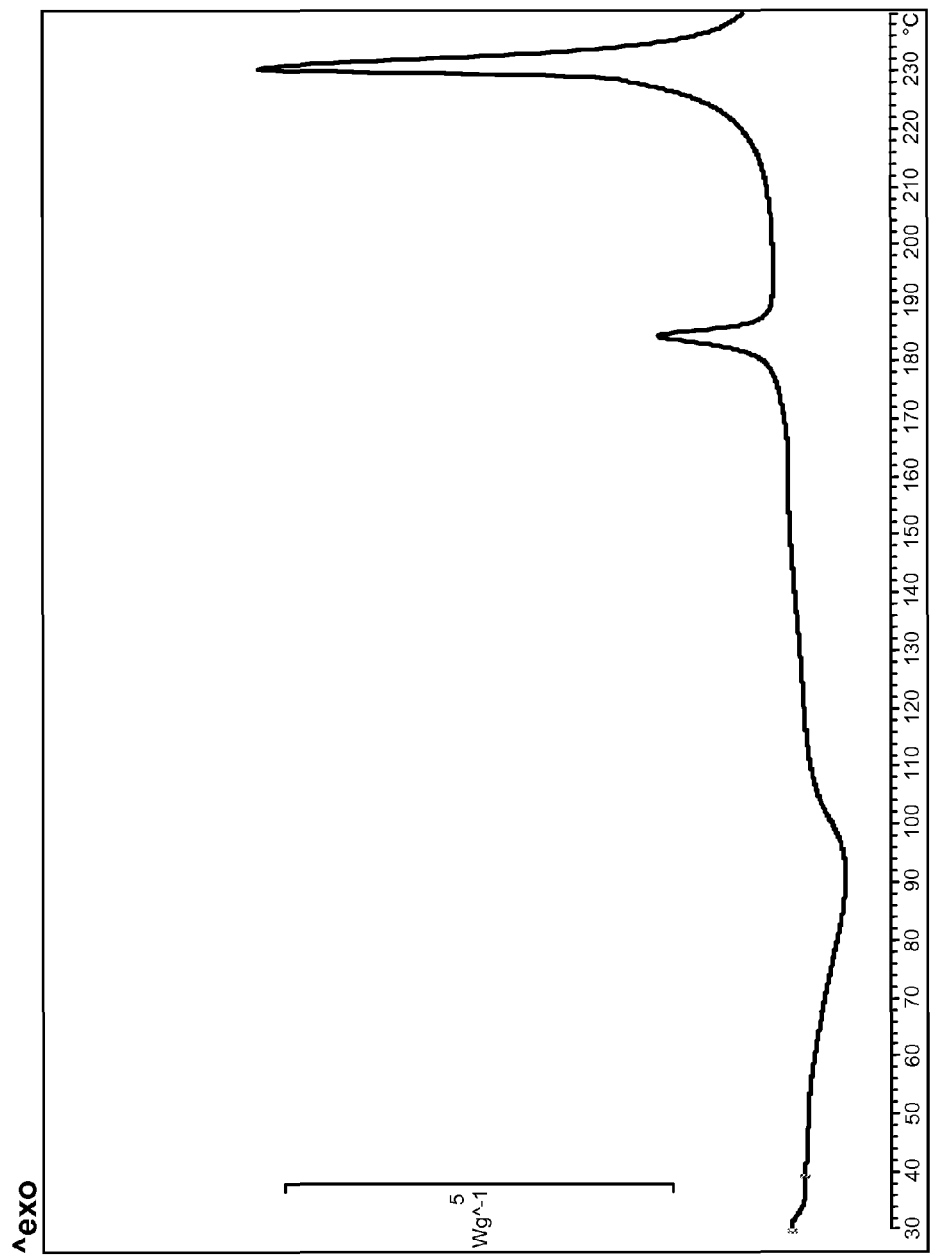
FIG. 5 shows a DSC curve of esomeprazole sodium Form P.

DSC analysis of Form P shows broad an endothermic transformation between 60 and 110° C., which may show evaporation of solvents, optionally desolvatation, and an exothermic transformation between 175 and 190° C. (FIG. 5).

The new crystal form comprising methanol, in particular the preferred Form P contains considerable amounts of methanol which cannot be removed by routine drying. The crystals cannot be considered as simply wet product because methanol is an essential factor of crystal structure keeping. But the percentage of methanol varies in a considerable extent and cannot be represented in a digit number of equivalents; therefore this composition could be denoted more as an adduct, rather than a solvate. The determined amount of methanol in the dried product is 5-15%, preferably 8-10%. But when the content of methanol drops to low values crystal structure collapsed and the physical form changes.

During the preparation of methanol-containing esomeprazole sodium such as Form P an antisolvent can be added in order to improve product yield. Surprisingly some antisolvents, especially those which are selected from the group of esters and ethers, preferably from methyl tert-butyl ether, diethyl ether and ethyl acetate, do not change crystal form and keep the content of methanol in the aforementioned, desired interval. But some other antisolvents, for example those selected from ketones, lead to products of less defined mixtures of various forms; for example an addition of acetone leads to a product which shows elements of Forms J and K in the diffractogram and which has a low determined amount of methanol. Such solvents should be avoided in order to keep reproducibility of the process.

Removal of methanol can be performed by drying in wet atmosphere. The product can be put into a drying chamber. Preferably, the chamber is not closed but slight flow of nitrogen which has previously been saturated with water vapours is blown through the chamber for at least 6 hours. After that the product is preferably dried again for some additional time under reduced pressure at temperature below 35° C.

During the process of wet drying the methanol-containing forms of esomeprazole sodium according to the invention such as Form P substantially loses degree of crystallinity. But surprisingly when a substantial amount or most or almost all of methanol is removed, the product is not completely amorphous but it shows a single high peak, wherein the specifically obtained Form Q has a high peak at 5.7 degrees of 2θ in XRD diffractogram. An amorphous state is characterized by an unordered arrangement of molecules in the solid state. The condition is similar to liquid state but with less flexibility of molecules. But in many cases an amorphous state shows a slight degree of ordering of molecules. States between amorphous and crystalline are therefore continuous. In the case of the invention such apparent intermediate state can be denoted as "semicrystalline" one. The semicrystalline state does not mean a mixture of crystalline and amorphous mass but that material shows a certain, usually a little degree of arrangement of molecules.

Figure 3:
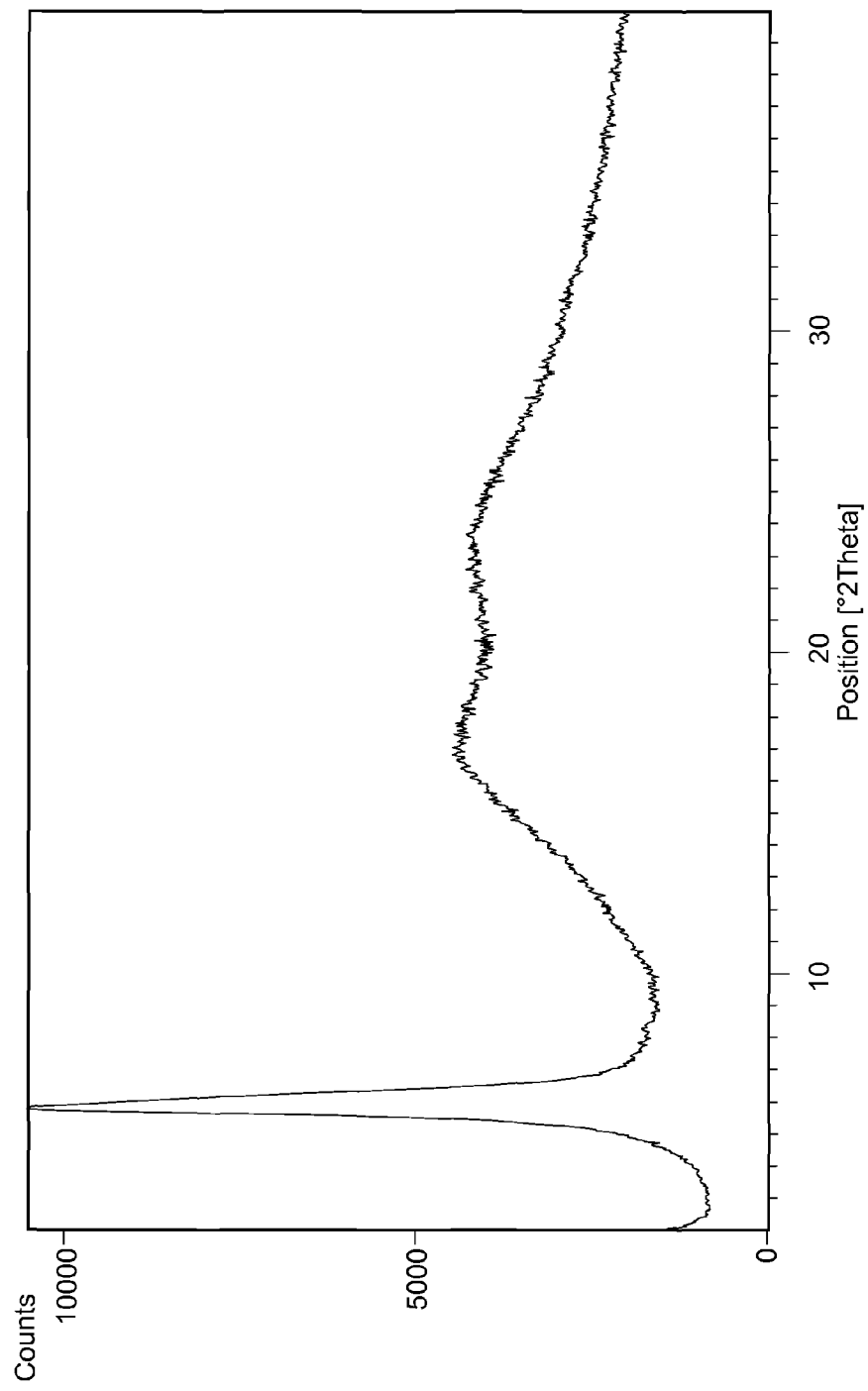
FIG. 3 is an X-Ray powder diffractogram of esomeprazole sodium Form Q.

The semicrystalline material which is obtained by wet drying of esomeprazole sodium of the specific Form P is here referred to as esomeprazole sodium Form Q and is characterized by a high peak 5.7 degrees of 2θ in XRD diffractogram while the rest of the curve is plain. The whole curve of Form Q is shown in FIG. 3. The product is neither a mixture of amorphous form and Form P nor badly crystalline Form P because the highest peak in Form Q is not the same as the highest peak of Form P, which becomes evident from a superposition of diffractograms. The product is also different from amorphous product prepared by prior art process (WO 94/027988)—see FIG. 4—or amorphous form shown in FIG. 6 of US 2007/0259921.

Figure 6:
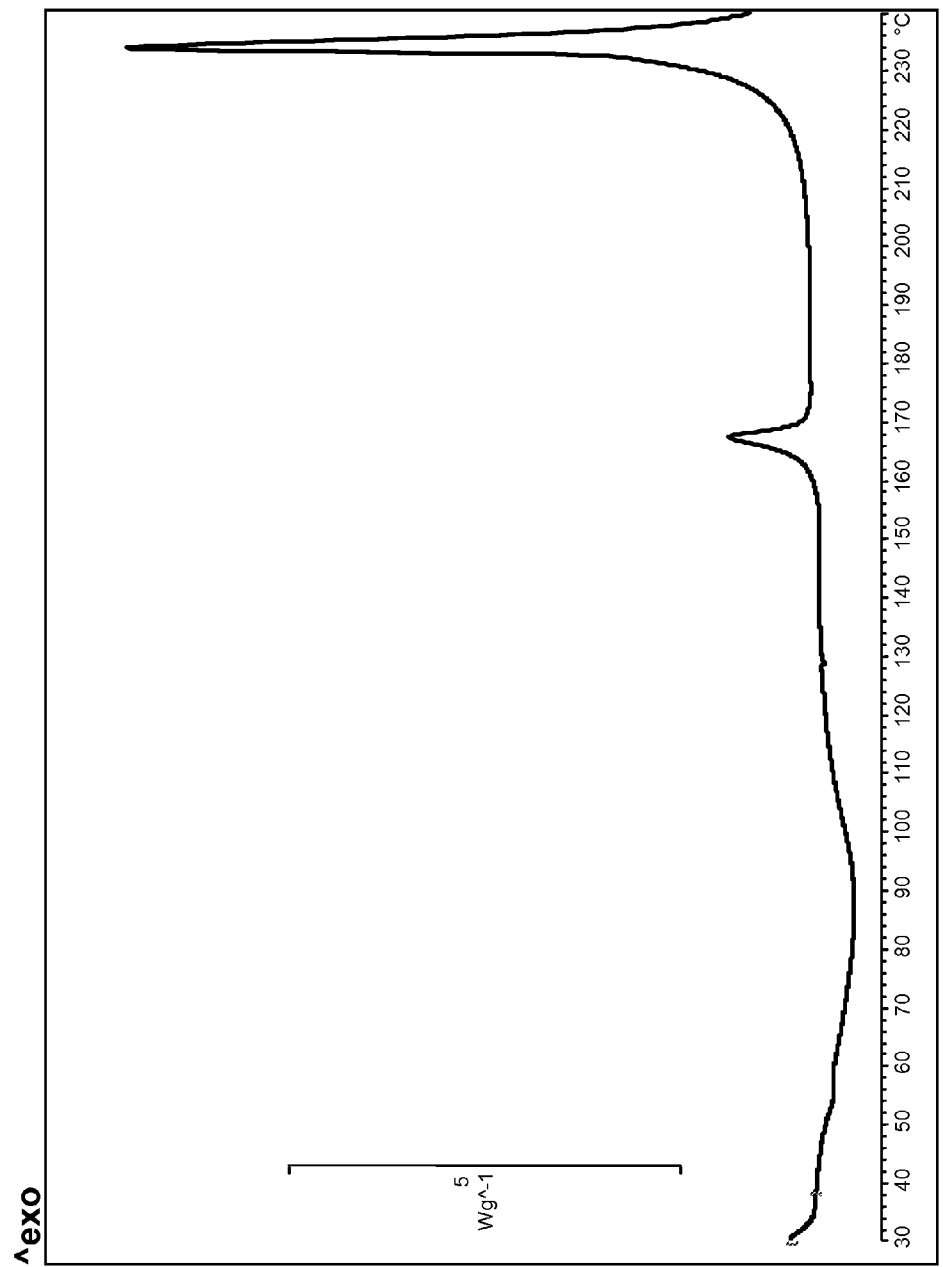
FIG. 6 shows a DSC curve of esomeprazole sodium Form Q.
Figure 7:
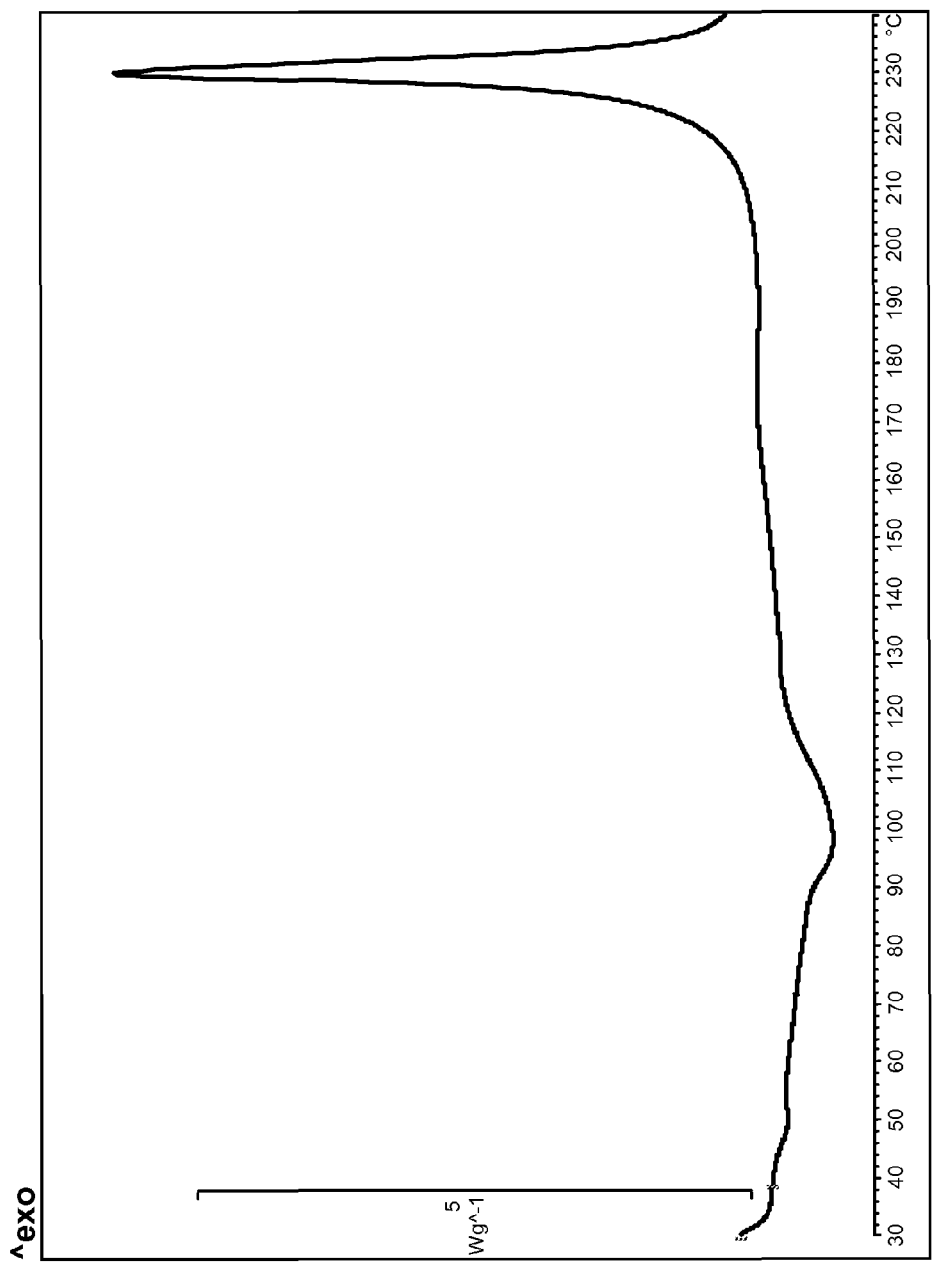
FIG. 7 shows a DSC curve of amorphous esomeprazole sodium, prepared according to prior art process.

DSC analysis of Form Q shows an endothermic transformation which may represent solvent evaporation, optionally glass transition state, then a exothermic transformation between 160 and 175° C. and exothermic degradation above 220° C., typical for all omeprazole forms (FIG. 6). Thermogram clearly differentiates from thermogram of the amorphous product prepared from 2-butanone/toluene mixture according to prior art (WO 94/027988), which does not show peaks between 150 to 200° C. (FIG. 7).

Esomeprazole sodium Form Q is prepared by drying of esomeprazole sodium Form P at reduced pressure, preferably between 5-20 milibars at temperature below 35° C. Further, gentle flow of nitrogen saturated by water vapour, optionally prepared by bubbling of nitrogen through water, is blown through the product. Wet drying is preferably carried out at room temperatures. The drying cycle describe above was repeat several times.

During this period the assay determination of methanol drops bellow 0.3% (limits of residual solvents defined in ICH-Q3C guideline, a key world-wide accepted guideline of quality directives for pharmaceutical ingredients) preferably bellow 0.1%. Water content is about 1%.

Figure 2:
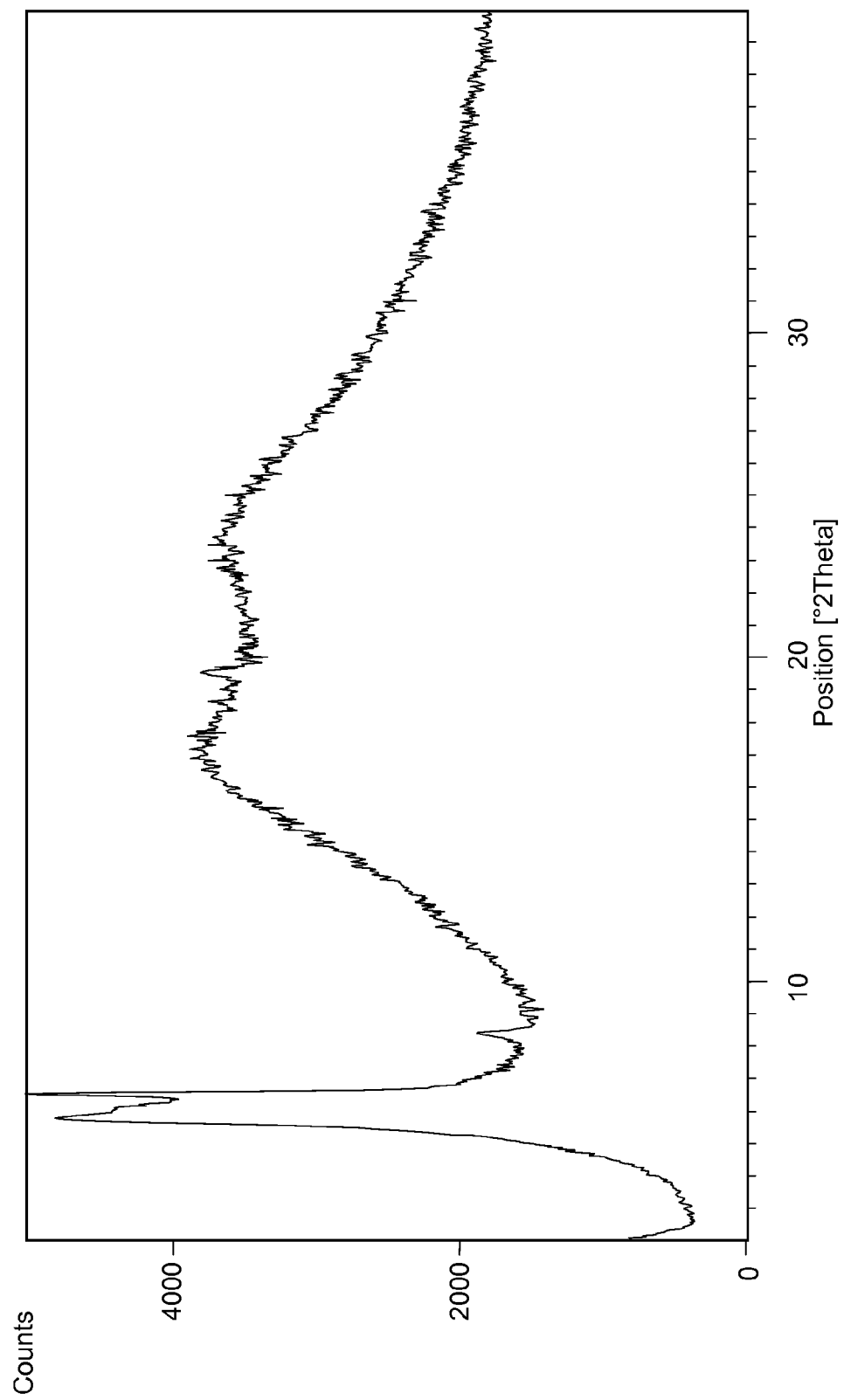
FIG. 2 is an X-Ray powder diffractogram of esomeprazole sodium Form Q and a mixture of crystal forms including Form P.

In an alternative embodiment, esomeprazole sodium Form Q is prepared by rapid precipitation from very concentrated methanolic solutions. In one aspect the Form Q is obtained by additional concentration of methanolic mother liquors after Form P preparation. In another aspect Form Q is prepared by rapid addition of higher quantities of an antisolvent selected from ethers or esters. From the products obtained by such procedures methanol can be removed to levels below 5% by classical drying at reduced pressure. Products obtained by this process contain Form but usually in admixture with Form P or with other not identified forms, what is shown by additional peaks in diffractograms, illustrated in FIG. 2.

In another embodiment, more clear precipitation Form Q directly without intermediate isolation of Form P is performed by treating methanol solution with ultrasound all the time during nucleation, crystallisation and before filtration. Thus esomeprazole is reacted with sodium source in methanol as described above and the obtained solution is stirred at a temperature between 15° C.-30° C., allowing esomeprazole sodium salt to form (0.5-1 h). The solution containing esomeprazole sodium salt was evaporated at a temperature below 40° C., until concentration of esomeprazole in solution was between 250-300 g/L. Then the mixture is treated by ultrasound all the time during crystallisation, preferably below 10° C. for some time, preferably 3-4 hours, then the precipitate is isolated as described above. Physico-chemical analyses show Form Q, identical as described above.

According to a comprehensive description of the invention the most preferred but not limiting procedure of preparation of esomeprazole of high chemical purity includes the following steps:

- Starting with neutral omeprazole with at least 99.90% of chemical purity
- Separating off R-enantiomer in PHPLC column with ChiralPak AD, 20 μm particle size as stationary phase, methanol as mobile phase and addition of diethylamine into uploading sample in order to obtain S-enantiomer with at least 99.7% of enantiomeric purity and at least 99.95% of chemical purity
- Concentrating eluate to 100 to 300 g of esomeprazole per litre
- Adding about 0.90 to about 1.50 eq, for example around 1.05 eq of sodium hydroxide in methanol solution and stirring the obtained mixture for 0.5 to 1 hour at room temperature
- Concentrating the mixture below a concentration of 250 g esomeprazole sodium per litre and cooling the mixture to −10° C., optionally adding a new solvent selected from ethyl acetate, methyl tert-butyl ether or diethyl ether and stirring the mixture for further 0.5 to 1 hours at the same temperature
- Filtering off the precipitate, and washing it with methanol or the second solvent to obtain obtained methanol wet sodium esomeprazole which is substantially free of inorganic impurities
- Drying the precipitate at reduced pressure at 30-40° C. to constant weight to give white coloured esomeprazole sodium Form P with methanol content 8-15% and at least 99.95% of chemical purity
- Drying the obtained crystals at reduced pressure and in the flow of nitrogen saturated with water vapour at 30-40° C. to give white coloured semicrystalline esomeprazole sodium Form Q with methanol content below 0.3% and at least 99.95% of chemical purity.

It is known that omeprazole is a useful proton pump inhibitor and can be used for the control of gastric acid secretion in mammals and especially in man. In particular, the novel esomeprazole sodium forms described herein and in particular Form Q may be used for prevention and the treatment of gastric-acid related conditions and inflammatory diseases, including for example, reflux esophagitis, gastritis, duodenal ulcer, non ulcer dyspepsia, upper gastrointestinal bleeding, stress ulceration, gastronomas, co-administration of patients on NSAID therapy, and pre-operative and post-operative treatment schemes to prevent aspiration of gastric acid. Further, esomeprazole sodium Form Q may be useful in the treatment of psoriasis and in the treatment of Helicobacter infections and diseases related to these.

The preparation of a pharmaceutical compositions containing the novel esomeprazole sodium forms described herein and in particular Form Q of high purity and pharmaceutically acceptable excipients is also an aspect of the present invention. The pharmaceutical composition of the invention is suitable for oral and parenteral administration. The most suitable route of administration as well magnitude of a therapeutic dose of omeprazole sodium according to the invention in any given case will depend on the nature and severity of the disease to be treated. The dose and dose frequency may also vary according to the age, body weight, and response of the individual patient. In general, a suitable dose of the active ingredient is within the range of 10 mg to 80 mg daily, preferably between 20 to 40 mg of total daily dosage. Dosage forms include capsules, tablets, dispersions, solutions, suspensions, emulsions, gels, powders, wherein the most preferred dosage forms of esomeprazole sodium Form Q are dry powder injections and infusions. In a most preferred embodiment the novel esomeprazole sodium forms described herein and in particular Form Q is dissolved in sterile and apyrogen water together with stabilisers, buffers, and additives, and the mixture is lyophylised to give vials of amorphous powder which is dissolved in prepared liquid just before use.

The following examples illustrate the process of the present invention and are not intended to limit the scope of the invention set forth in the claims appended hereto.

Example 1

Preparation of Neutral Esomeprazole

Neutral racemic omeprazole of chemical purity of 99.91% (commercially available) was dissolved in 0.005% solution of diethylamine in methanol (24 g omeprazole per L) and the solution was loaded to column (ChiralPak AD, 20 μm particle size, column length 350 mm). Products were eluted by methanol and S-enantiomer was collected first. The prepared solution was injected several times to the top of chromatographic column until the wanted quantity was obtaining. The collected main fractions were evaporated at the temperature below 40° C. under reduced pressure until the concentration of 100-300 g/l of active substance was reached.

Example 2

Preparation of Esomeprazole Sodium Form P 16 g of sodium hydroxide was dissolved in methanol (320 ml). The obtained solution was added to 550 ml of esomeprazole concentrate (containing 130 g of esomeprazole), obtained as described in Example 1.

The reaction mixture was stirred at the temperature between 15° C.-30° C. allowing esomeprazole sodium salt to form (reaction time 0.5-1 h). The solution containing esomeprazole sodium salt was concentrated by evaporation at the temperature below 40° C. under reduced pressure until the concentration of 250 g/l of active substance was reached. The solution was cooled to 15° C. and stirred at the same temperature for another hour allowing esomeprazole sodium salt to crystallise. The crystals were filtered off by vacuum filtration. The obtained product was dried at the temperature below 35° C. under reduced pressure to get 68 g of esomeprazole sodium of Form P as presented by XRD diffractogram in FIG. 1 (99.95% of chromatographic purity, methanol 12.9% (w/w)).

Example 3

Preparation of Esomeprazole Sodium Form P 15 g of sodium hydroxide was dissolved in methanol (300 ml). The obtained solution was added to 650 ml of esomeprazole concentrate (containing 130 g of esomeprazole) obtained as described in Example 1.

The reaction mixture was stirred at the temperature between 15° C.-30° C. allowing esomeprazole sodium salt to form (reaction time 0.5-1 h). The solution containing esomeprazole sodium salt was cooled to −5° C. and seeded with a 0.04 g of esomeprazole sodium obtained in Example 2. The formed suspension was cooled to −10° C. and stirred at the same temperature overnight. The crystals were filtered off by vacuum filtration. The obtained product was dried at the temperature below 35° C. under reduced pressure to get 61 g of esomeprazole sodium Form P with identical XRD diffractogram as in Example 2 (100.0 area % chromatographic purity, methanol 10.0% (w/w)).

Example 4

Preparation of the Second Crop of Esomeprazole Sodium

Liquors, obtained after isolation of sodium salt in Example 2, were cooled to −15° C. and seeded with a 0.04 g of esomeprazole sodium obtained in Example 2. The formed suspension was cooled to −20° C. and stirred for another 1.5 hours at the same temperature. The crystals were with filtered off by vacuum filtration and filer cake was washed with ethyl acetate (EtOAc). The obtained product was dried at the temperature below 35° C. under reduced pressure to get 16 g of esomeprazole sodium, solid form presented by XRD diffractogram in FIG. 2 (99.95% chromatographic purity, methanol 0.74% (w/w), EtOAc 0.47% (w/w)).

Example 5

Preparation of Esomeprazole Sodium Form P 11.6 g of sodium hydroxide was dissolved in methanol (232 ml). The obtained solution was added to 700 ml of esomeprazole concentrate (containing 100 g of esomeprazole) obtained as described in Example 1.

The reaction mixture was stirred at the temperature between 15° C.-30° C. allowing esomeprazole sodium salt to form (reaction time: 0.5-1 h). The solution containing esomeprazole sodium salt was evaporated at temperature bellow 40° C. until concentration of esomeprazole in solution was about 500 g/L. Methyl tert-butyl ether (MTBE) was added to the mixture (800 ml). The formed suspension was cooled to 0° C. and stirred at same temperature for another hour.

The crystals were filtered off by vacuum filtration. The obtained product was washed with MTBE and dried at the temperature below 35° C. under reduced pressure to get 105 g of esomeprazole sodium Form P with identical XRD diffractogram as in Example 2 (100.0% of chromatographic purity, sodium 6.3% per dry substance, methanol 13.6% (w/w), MTBE 0.1% (w/w)).

Example 6

Preparation of Esomeprazole Sodium Form P 11.6 g of sodium hydroxide was dissolved in methanol (232 ml). The obtained solution was added to 700 ml of esomeprazole concentrate (containing 100 g of esomeprazole), obtained as described in Example 1.

The reaction mixture was stirred at the temperature between 15° C.-30° C. allowing esomeprazole sodium salt to form (0.5-1 h). The solution containing esomeprazole sodium salt was evaporated at temperature bellow 40° C. until concentration of esomeprazole in solution was about 588 g/L. EtOAc was added to the mixture (800 ml). The formed suspension was cooled to 0° C. and stirred at same temperature for 2 hours.

The crystals were filtered off by vacuum filtration. The obtained product was washed with EtOAc and dried at the temperature below 35° C. under reduced pressure to get 93 g of esomeprazole sodium Form P with identical XRD diffractogram as in Example 2 (100.0% of chromatographic purity, sodium 6.4% per dry substance, methanol 10.8% (w/w), EtOAc 0.4% (w/w))

Example 7

Preparation of Esomeprazole Sodium Form P 10.9 g of sodium hydroxide was dissolved in methanol (218 ml). The obtained solution was added to 400 ml of esomeprazole concentrate (containing 94 g of esomeprazole), obtained as described in Example 1.

The reaction mixture was stirred at the temperature between 15-30° C. allowing esomeprazole sodium salt to form (0.5-1 h). The solution containing esomeprazole sodium salt was evaporated at temperature bellow 40° C. until concentration of esomeprazole in solution was about 700 g/L. Diethyl ether (DEE) was added to the mixture (700 ml). The formed suspension was cooled to 0° C. and stirred at same temperature overnight.

The crystals were filtered off by vacuum filtration. The obtained product was washed with DEE and dried at the temperature below 35° C. under reduced pressure to get 85 g of esomeprazole sodium Form P with slight amounts of form Q according to XRPD diffractogram (99.9% of chromatographic purity, sodium 6.5% per dry substance, methanol 9.5% (w/w), DEE 0.04% (w/w))

Example 8

Preparation of Esomeprazole Sodium Form Q 60 g of esomeprazole sodium (containing 10.0% (w/w) of methanol) from Example 3 was further dried for 4 days at 35° C. in vacuum in order to reduce residual solvents. After 4 days drying the residual solvents content was approximately 9.5% (w/w) of methanol.

Further, nitrogen saturated with water at 40° C. was blown through the product for at least 6 hours and dried for some additional time (10-16 hours) in vacuum at 35° C. The drying cycle described above was repeated twice. The residual methanol content was decreased below 0.5% (w/w), yielding esomeprazole Form Q, diffractogram presented in FIG. 3.

Example 9

Preparation of Esomeprazole Sodium Form Q 105 g of esomeprazole sodium (containing 13.5% (w/w) of methanol) from Example 5 was further dried for 4 days at 35° C. in vacuum in order to reduce residual solvents. After 4 days drying the residual solvents content was approximately 12.3% (w/w) of methanol.

Further, nitrogen saturated with water at 40° C. was blown through the product for at least 6 hours and dried for some additional time (10-16 hours) in vacuum at 35° C. The drying cycle described above was repeated twice. The residual methanol content was decreased below 0.5% (w/w), yielding esomeprazole Form Q according to XRPD.

Example 10

84.8 g of esomeprazole sodium (containing 9.5% (w/w) of methanol) from Example 7 was further dried for 4 days at 35° C. in vacuum in order to reduce residual solvents. After 4 days drying the residual solvents content was approximately 9.2% (w/w) of methanol.

Further, nitrogen saturated with water at 40° C. was blown through the product for at least 6 hours and dried for some additional time (10-16 hours) in vacuum at 35° C. The drying cycle described above was repeated twice. The residual methanol content was decreased below 0.5% (w/w), yielding esomeprazole Form Q according to XRPD.

Reference Example A

Figure 4:
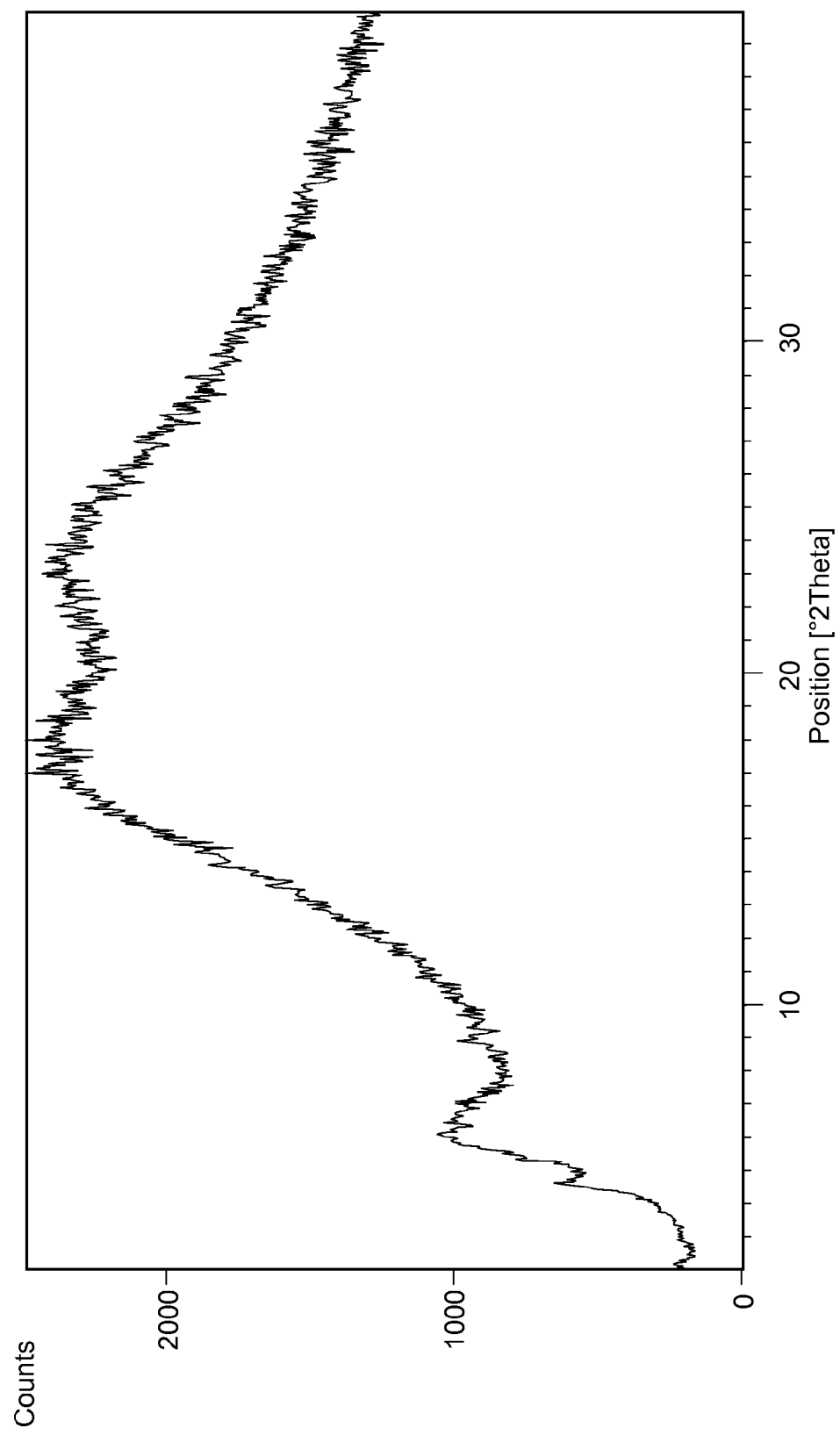
FIG. 4 is an X-Ray powder diffractogram of amorphous esomeprazole sodium, prepared according to prior art process.

Amorphous esomeprazole sodium was prepared according to Example 1 of WO 94/27988. XPRD diffractogram in FIG. 4 shows completely amorphous material.

Methods of Analysis

The products were analyzed by following methods:

X-Ray powder diffraction method:

Conditions for obtaining powder X-ray diffraction (XRD) patterns: the powder X-ray diffraction patterns were obtained by methods known in the art using Philips X'Pert PRO diffractometer with X'Celerator detector using CuKa radiation (tube operating at 45 kV and 40 mA) in the Bragg-Brentano (reflection) geometry. Data were recorded from 2 to 40° 2θ in steps of 0.033° 2θ and the measurement time of 50 seconds per step. Variable divergence and antiscatter slits were used to maintain 12 mm of sample length irradiated.

Differential Scanning Calorimetry:

Conditions for obtaining DSC thermograms: Thermograms were obtained with Mettler Toledo DSC822e differential scanning calorimeter. The sample (4-6 mg) was placed in an unsealed aluminium pan with a hole and heated at 5° C./min in the temperature range from 30° C. to 200° C.

Methanol Determination Assay:

Principle: Gradient GC determination of residual solvents using headspace method of external standard.

Instrument: GC Agilent 6890N equipped with Agilent G1888 Headspace sampler

Column: DB-624 (6%-cyanopropyl-phenyl-94%-dimethylpolysiloxane), 30 m×0.32 mm I.D.×1.8 mm film thickness Injector: Split ratio 20:1, T=250° C., Headspace Volatiles injection Detector: FID, T=300° C.

30 ml/min hydrogen 400 ml/min air 25 ml/min makeup gas (nitrogen)

Carrier gas: Helium, constant pressure 9.5 psi (initial flow 2 ml/min)

Temperature gradient: 40° C. (10 min)→30° C./min→240° C. (5 min).

The invention claimed is:

1. A form of esomeprazole sodium, which is semicrystalline by showing in an XRD diffractogram a single significant peak at a 2θ value of 5.7±0.2 degrees while the rest of the curve is plain without significant peaks.

2. The form of esomeprazole sodium according to claim 1, defined by a HPLC purity of 99.00% or higher.

3. The form of esomeprazole sodium according to claim 2, defined by a HPLC purity of 99.90% or higher or 99.95% or higher.

4. The form of esomeprazole sodium according to claim 3, wherein the pure esomeprazole sodium is defined by chemical or chromatographic (area % HPLC) purity of 99.00% or higher, or 99.90% or higher, or 99.95% or higher, and/or by a solvent level below 0.5% (w/w).

* * * * *